United States Patent [19]
Staudenmaier et al.

[11] Patent Number: 5,955,328
[45] Date of Patent: *Sep. 21, 1999

[54] FERMENTATIVE PREPARATION OF 2,5-DIHYDROXYPHENYLACETIC ACID WITH BEAUVERIA

[75] Inventors: Horst Ralf Staudenmaier, Limburgerhof; Bernhard Hauer, Fussgoenheim; Wolfgang Ladner, Fussgoenheim; Ursula Mueller, Fussgoenheim; Uwe Pressler, Altrip; Joachim Meyer, Maxdorf, all of Germany

[73] Assignee: BASF Aktiengesellschaft, Ludwigshafen, Germany

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/586,574

[22] Filed: Jan. 16, 1996

Related U.S. Application Data

[62] Continuation of application No. 08/409,962, Mar. 24, 1995, abandoned, which is a continuation of application No. 08/211,450, filed as application No. PCT/EP92/02222, Sep. 25, 1992, abandoned.

[30] Foreign Application Priority Data

Oct. 22, 1991 [DE] Germany ............... 41 34 774

[51] Int. Cl.$^6$ ...................................... C12P 7/42
[52] U.S. Cl. ............... 435/146; 435/132; 435/911; 435/136
[58] Field of Search ................... 435/146, 136, 435/132, 911

[56] References Cited

FOREIGN PATENT DOCUMENTS

| | | |
|---|---|---|
| 089 039 | 9/1983 | European Pat. Off. . |
| 343 330 | 11/1989 | European Pat. Off. . |
| AS 6633 | 3/1969 | Japan . |
| 11362 | 10/1990 | WIPO . |

OTHER PUBLICATIONS

Kieslich, K, "Microbial transformations of Non–Steriod Cyclic Compounds", 1976, pp. 107–108.

Holland, H. Organic Synthesis with Oxidative Enzymes, pp. 72–74, 1992.

ATCC Catalogue of Fungi, 1991 pp. 74–76.

Sugumaran, et al., FEMS Microbiol. Lett, 5, 1976, pp. 427–430.

Boyd et al., J. Chem Soc Perk. Trans(1976)(22) pp. 2438–2443.

Sikyta, B, "Methods in Industrial Microbiology" 1983, pp. 230–235.

Bocks, *Phytochemistry*, 1967, vol. 6 pp. 785–789.

Yoshizako et al. (Agric. Biol. Chem. 49 (3) 1985, 877–879).

*Primary Examiner*—Irene Marx
*Attorney, Agent, or Firm*—Keil & Weinkauf

[57] ABSTRACT

The present invention relates to a novel process for the preparation, by fermentation, of compounds of the formula I

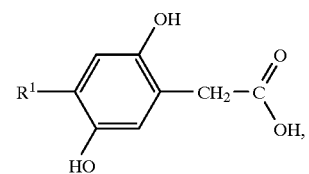

where $R^1$ is hydrogen, fluorine, chlorine or bromine.

2 Claims, No Drawings

FERMENTATIVE PREPARATION OF 2,5-DIHYDROXYPHENYLACETIC ACID WITH BEAUVERIA

This application is a continuation of application Ser. No. 08/409,962, filed on Mar. 24, 1995, abandoned which is a continuation of application Ser. No. 08/211,450, filed on Mar. 31, 1994 abandoned which was filed under 35 USC 371 as the national phase of PCT EP/92/02222 filed Sep. 25, 1992.

The present invention relates to a novel process for the preparation, by fermentation, of a compound of the formula I

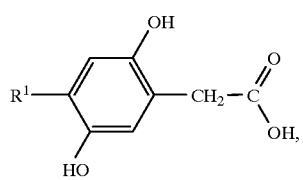

where $R^1$ is hydrogen, fluorine, chlorine or bromine.

Compounds of the formula I are valuable intermediates in the preparation of dyes and pharmaceuticals.

In particular, 2,5-dihydroxyphenylacetic acid (homogentisic acid) is used as photographic developer, for cosmetic products and for preparing pharmaceuticals.

It is known that microorganisms are able to hydroxylate aromatic compounds. The hydroxylation of the aromatic ring in many cases represents the first step in a sequence of reactions which leads to the breakdown of the relevant substance.

Yoshizako et al. (Agric. Biol. Chem. 49 (3), 1985, 877–879) disclose that the breakdown of phenylacetic acid in various fungi takes place via the intermediate 2,5-dihydroxyphenylacetic acid (homogentisic acid). These fungi include, for example, those of the genera Aspergillus, Fusarium, Gibberella, Mucor, Pellicularia, Penicillium, Phellinus and Rhizopus. However, only very small amounts of homogentisic acid are produced as metabolite of phenylacetic acid because it is usually further broken down by cleavage of the aromatic ring. Wild-type strains are therefore unsuitable for production of homogentisic acid for economic reasons.

JP-B 6633/69 describes a process for preparing homogentisic acid from phenylacetic acid by aerobic culturing of an artificially produced variant of Penicillium chrysogenum. The process specified in Example 1 therein gives a yield of 47% of homogentisic acid from phenylacetic acid, which was present in a cumulative concentration of 5 g/l. Necessary for an economic process are, on the one hand, a high yield and, on the other hand, as high a substrate concentration in the medium as possible.

It is an object of the present invention to provide a fermentation process for preparing compounds of the formula I which provides good yields and makes high substrate concentrations possible.

We have found that this object is achieved by the process, defined in the first paragraph, for the preparation, by fermentation, of compounds of the formula I

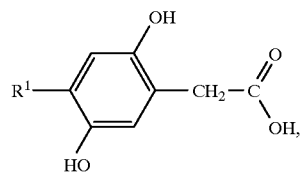

where $R^1$ is hydrogen, fluorine, chlorine or bromine, which provides particularly good yields when compounds of the formula II

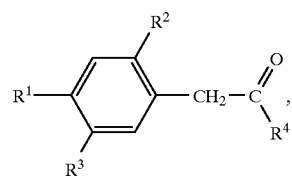

in which $R^1$ has the abovementioned meanings, $R^2$ and $R^3$ are each, independently of one another, hydrogen, hydroxyl or methoxy and $R^4$ is hydroxyl, methoxy or amino, are hydroxylated in the presence of a microorganism of the genus Aspergillus or Beauveria which is able to hydroxylate, but not utilize as C source, compounds of the formula II. The fungus Beauveria bassiana has been deposited in accordance with the Budapest treaty under the accession number given by the International Depositary Authority of DSM 6650. The name of the depository is the Deutsche Sammlung von Mikroorganismen und Zellkulturen Gmbh, located at Mascheroder Weg 1 B, D-3300 Braunschweig. The deposit was made in Aug. 6, 1991.

The starting compounds of the formula II required for the process according to the invention are known.

They can be prepared, for example, by the processes described in Houben-Weyl, Methoden der organischen Chemie, Volume 8.

The conversion of the abovementioned starting compounds into compounds of the formula I by microorganisms comprises a hydroxylation of the aromatic nucleus in positions 2 and 5. When there is hydrogen or methoxy in these positions in the starting compound, this radical is replaced by hydroxyl in the process according to the invention.

Radicals in position 4 of the aromatic nucleus, such as hydrogen or halogen, are unchanged in the process according to the invention. Starting compounds which are preferably used have hydrogen in position 4.

Besides hydroxylation on the aromatic ring, the process according to the invention may also result in a modification of the carboxyl. Thus, for example, a methyl ester or an amide is converted into the free acid or its salt. If a free acid or its salt is used as starting compound, this group is not altered by the process.

The microorganisms suitable for the process according to the invention on the one hand must have the ability to hydroxylate the starting compounds on the aromatic nucleus, but on the other hand they must not utilize the starting compound as carbon source.

Microorganisms of this type are expediently obtained by mutation of wild-type strains which have the ability to hydroxylate aromatic rings.

Preferably used as microorganisms are those of the genus Aspergillus or Beauveria, for example *Aspergillus niger*. Particularly preferred are those of the species *Beauveria bassiana* DSM 6650.

It is easy to establish whether a microorganism is suitable for hydroxylating the starting compound in the required manner on the aromatic nucleus with the aid of analytical methods, eg. gas chromatography, using the nutrient medium.

The starting compound to be hydroxylated is expediently added to the nutrient medium and, during the course of cultivation, it is examined to find whether the starting compound decreases and the required hydroxylated compound occurs as metabolite. Metabolites can be identified by conventional methods such as resting cell experiments, use of inhibitors or isotope labeling.

The mutants generated from the suitable microorganisms are expediently no longer able to use the starting compound as carbon source.

Known microbiological techniques can be employed to generate such mutants. All conventional methods can be used to induce mutations, such as the use of mutagenic substances, eg. nitrosoguanidine, ethyl methanesulfonate, sodium nitrite, or exposure to electromagnetic radiation such as UV, gamma or X-rays. It is also possible to use transposable genetic elements for the mutagenesis. Various properties can be utilized to isolate the mutants, such as the inability to grow on phenylacetic acid as sole C source or the visually evident brown coloration resulting from the homogentisic acid produced. It is possible at this point, if necessary, also to carry out an enrichment of the mutants which are sought.

The process according to the invention is carried out with suitable microorganisms which are cultivated in a nutrient medium which contains the starting compound in a concentration of from 1 to 20 g/l, preferably from 5 to 15 g/l.

The process according to the invention is preferably carried out with replacement of used substrate by metering in a highly concentrated stock solution of substrate. It is possible in this way to achieve cumulative substrate concentrations of up to 50 g/l in the fermentation medium.

The cultivation time depends on the starting compound and the microorganism; as a rule it is a few days. The cultivation is expediently continued until there is virtually quantitative conversion of the starting compound.

The cultivation can be carried out in a continuous or batchwise process; however, a batchwise procedure is preferred.

The hydroxylated phenylacetic acid can be isolated and purified from the nutrient medium by conventional methods. It is expedient to separate the solid biomass from the nutrient medium, to extract the required product, eg. with an organic solvent, and to isolate it from the extracted phase, if necessary after further purification, eg. by crystallization.

The invention is further explained by the examples which follow.

EXAMPLE 1

Preparation of a Mutant (Lu 6577) of *Beauveria bassiana*

The fungus *Beauveria bassiana* DSM 6650 was mutated using N-methyl-N'-nitro-N-nitrosoguanidine (MNNG). A suspension of fungal spores in 0.1 M phosphate buffer pH 7.0, 0.1% by weight polyethoxysorbitan oleate (Tween® 80) was adjusted to a titer of $10^7$ spores per ml. 10 ml of this spore suspension were adjusted to a concentration of 0.2 mg/ml MNNG by addition of a stock solution of 5 mg/ml MNNG (dissolved in dimethylformamide), and incubated at 30° C., shaking gently, for 15 min. The spores were then harvested by centrifugation (5,000 rpm for 5 minutes) and washed twice with 10 ml Tween buffer. The spores were taken up in Tween buffer, diluted and plated out on complex medium. Comparison with untreated spores regularly showed in several experiments a survival rate of from 1 to 2% for the mutated spores.

The mutated spores were plated out on agar plates containing complex medium of the following composition and incubated at 30° C. for 5 days:

| | |
|---|---|
| 50 g/l | D-glucose |
| 10 g/l | yeast extract |
| 3.6 g/l | $K_2HPO_4$ |
| 1.5 g/l | $KH_2PO_4$ |
| 0.5 g/l | $MgSO_4 \times 7\ H_2O$ |
| 0.05 g/l | $MnSO_4 \times H_2O$ |
| 2 ml/l | trace element solution |
| 20 g/l | agar |

Trace element solution;

| | |
|---|---|
| 200 mg/l | iron(II) sulfate monohydrate |
| 10 mg/l | zinc(II) sulfate tetrahydrate |
| 3 mg/l | manganese chloride tetrahydrate |
| 30 mg/l | boric acid |
| 20 mg/l | cobalt(II) chloride hexahydrate |
| 1 mg/l | copper(II) chloride dihydrate |
| 2 mg/l | nickel(II) chloride hexahydrate |
| 3 mg/l | sodium molybdate dihydrate |
| 500 mg/l | ethylenediaminetetraacetic acid (EDTA) |

Toothpicks were used to inoculate a small piece of mycelium from the resulting single colonies into test tubes each containing 2 ml of the following minimal medium with phenylacetic acid as sole carbon source:

| | |
|---|---|
| 5 g/l | phenylacetic acid |
| 5 g/l | $(NH_4)_2SO_4$ |
| 3.6 g/l | $K_2HPO_4$ |
| 1.5 g/l | $KH_2PO_4$ |
| 0.5 g/l | $MgSO_4 \times 7\ H_2O$ |
| 0.05 g/l | $MnSO_4 \times H_2O$ |
| 2 ml/l | trace element solution |

The mixtures were shaken (180 rpm) at 30° C. for 7 days. Clones which had not grown densely on the medium during this period were further characterized. The proportions of clones which did not grow ranged from 3 to 8% in various experiments.

The clones to be further characterized were inoculated from the retained sample into 2 ml of complex medium containing 2 g/l phenylacetic acid in each case, and cultivated with shaking at 30° C. for 10 days.

The cultures were then centrifuged and a photometric assay was carried out on the culture supernatant: 0.5 ml of 1.6% $NaNO_2$ and 0.2 ml of 1 M $H_2SO_4$ were added to 0.5 ml of culture supernatant and incubated for 10 min. Then 0.25 ml of 0.2% by weight EDTA in 2.3 M NaOH was added and the samples were measured at 450 nm with the blank as reference. For the blank, water in place of $NaNO_2$ solution was added, otherwise the procedure was the same.

Clones which had an extinction $A_{450}>1.8$ in the photometric assay (1–5% of the assayed clones) were further investigated in shaken flask experiments. For this in each case a preculture of the clones was made up in complex medium containing 2.5 g/l phenylacetic acid (30 ml in 250 ml Erlenmeyer flasks). After shaking at 30° C. for 3 days, 5 ml portions of the preculture were used to inoculate a main culture containing 10 g/l phenylacetic acid, which was shaken at 30° C. A sample was taken after 3 and after 7 days and analysed for the content of phenylacetic acid and its derivatives by gas chromatography.

1 ml of the culture was removed, 100 μl of 5 M HCl and 800 μl of ethyl acetate were added, and the mixture was mixed for 15 s and centrifuged at 12,000 g for 2 min. 50 μl of the organic phase were removed and 50 μl of N-methyl-N-(trimethylsilyl)trifluoroacetamide (MSTFA) were added.

The samples were subjected to gas chromatography (165° C. isothermal, column: methylsilicone 12.5 m, Hewlett-Packard, 1 μl injected). In the chromatogram, phenylacetic acid appeared after 1.7 min and homogentisic acid after 7.8 min.

In this assay, the mutant Lu 6577 showed complete conversion of phenylacetic acid to homogentisic acid after 7 days.

EXAMPLE 2
Preparation of Homogentisic Acid from Phenylacetic Acid

The mutant Lu 6577 was inoculated into 5×30 ml of the following medium in 250 ml Erlenmeyer flasks and incubated aerobically, shaking at 180 rpm, at 30° C. for 3 days:

| | | |
|---|---|---|
| 2.5 g/l | phenylacetic acid | |
| 50 g/l | D-glucose | |
| 10 g/l | yeast extract | |
| 0.5 g/l | $MgSO_4 \times 7\ H_2O$ | |
| 1.5 g/l | $KH_2PO_4$ | |
| 3.6 g/l | $K_2HPO_4$ | |
| 2 ml/l | trace element solution | |

This preculture was used to inoculate a 1 l fermenter containing the same medium and a phenylacetic acid concentration of 10 g/l. The fermenter was stirred at 600 rpm and 1 volume of air per volume of the reactor was passed through per minute. Whenever the reaction had progressed until the phenylacetic acid concentration had fallen to 0.5–5 g/l, each time a 20% strength stock solution of phenylacetic acid in water was metered in to restore the phenylacetic acid concentration to 5–10 g/l in the medium. A total of 30 g of phenylacetic acid was reacted in this way. After this amount was reached, the culture was incubated further without metering in phenylacetic acid. When the phenylacetic acid had been completely converted into homogentisic acid, the cells were removed by centrifugation. The culture supernatant was adjusted to pH 2 with HCl and the resulting homogentisic acid was obtained by extraction with ethyl acetate.

EXAMPLE 3
Preparation of Homogentisic Acid from 2-hydroxyphenylacetic Acid

A preculture (30 ml) of the strain Lu 6577 was made up as in Example 2 but without phenylacetic acid. 5 ml of the preculture were used after 3 days to inoculate a main culture (30 ml) in the same medium containing 5 g/l 2-hydroxyphenylacetic acid. The 2-hydroxyphenylacetic acid was completely converted into homogentisic acid after shaking at 180 rpm and 30° C. for 4 days.

EXAMPLE 4
Preparation of Homogentisic Acid from 3-hydroxyphenylacetic Acid

A main culture of Lu 6577 was made up in the same way as in Example 3 with the difference that 1 g/l 3-hydroxyphenylacetic acid was added as substrate. The 3-hydroxyphenylacetic acid was converted into homogentisic acid after incubation with shaking at 30° C. for 4 days.

EXAMPLE 5
Preparation of Homogentisic Acid from 3-methoxyphenylacetic Acid

A main culture was inoculated with Lu 6577 as in Example 3. 1 g/l 3-methoxyphenylacetic acid was added as substrate. The substrate was demethylated to 3-hydroxyphenylacetic acid and then hydroxylated to homogentisic acid over the course of 4 days.

EXAMPLES 6 AND 7
Preparation of Halogenated hydroxyphenylacetic Acids

In each case a 10 l fermenter was inoculated with a preculture (3×330 ml) of the mutant Lu 6577 and incubated at 30° C. for 3 days as described in Example 2. The precursor concentration was 0.5 g/l in the preculture and 5 g/l in the main culture. The results of the experiments are shown in Table 1.

TABLE 1

Conversion of halogenated phenylacetic acids with Lu 6577

| Ex. | Precursor | Product | Amount of isol. prod. (g) | Fermentation time (days) |
|---|---|---|---|---|
| 6 | $R^1$ = Cl, $R^2$ = H, $R^3$ = H | $R^1$ = Cl, $R^2$ = OH, $R^3$ = OH | 30 | 8 |
| 7 | $R^1$ = F, $R^2$ = H, $R^3$ = H | $R^1$ = F, $R^2$ = OH, $R^3$ = OH | 10 | 13 |

Precursor and Product structures: $R^1$, $R^2$, $R^3$ substituted benzene ring with $-CH_2-COOH$ group.

We claim:

1. A process for the preparation of a compound of formula I

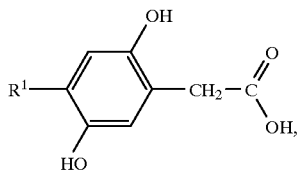

wherein $R^1$ is selected from the group consisting of hydrogen, fluorine, chlorine and bromine;

which process comprises cultivating a fungus of the genus Beauveria in a nutrient medium comprising a compound of formula II

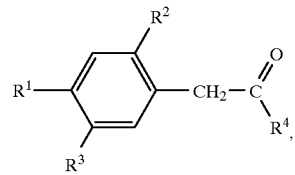

wherein $R^1$ has the abovementioned meanings; and $R^2$ and $R^3$ are, independently of each other, selected from the group consisting of hydrogen, hydroxy and methoxy; with the proviso that if $R^2$ is hydroxy, then $R^3$ is not hydroxy; and, with the further proviso that if $R^3$ is hydroxy, then $R^2$ is not hydroxy; and $R^4$ is selected from the group consisting of hydroxy, methoxy and amino; until the compound of formula I is produced;

said fungus of the genus Beauveria being unable to assimilate the compound of formula II as a C source; and recovering the compound of formula I.

2. A process as defined in claim 1, wherein the fungus of the genus Beauveria is *Beauveria bassiana* DSM 6650.

* * * * *